United States Patent [19]

Seidel

[11] Patent Number: 5,972,920
[45] Date of Patent: *Oct. 26, 1999

[54] FORMULATION CONTAINING A CARRIER, ACTIVE INGREDIENT, AND SURFACTANT FOR TREATING SKIN DISORDERS

[75] Inventor: William E. Seidel, Scarborough, Me.

[73] Assignee: Dermalogix Partners, Inc., Scarborough, Me.

[*] Notice: This patent issued on a continued prosecution application filed under 37 CFR 1.53(d), and is subject to the twenty year patent term provisions of 35 U.S.C. 154(a)(2).

[21] Appl. No.: 09/022,995

[22] Filed: Feb. 12, 1998

[51] Int. Cl.$^6$ .......................... A61K 31/56; A61K 31/60; A61K 31/555; A61K 33/04
[52] U.S. Cl. .......................... 514/171; 514/159; 514/178; 514/180; 514/181; 514/188; 514/762; 424/702; 424/705
[58] Field of Search ..................................... 514/171, 178, 514/180, 181, 188, 159, 762; 424/702, 705

[56] References Cited

U.S. PATENT DOCUMENTS

| | | |
|---|---|---|
| 3,730,182 | 5/1973 | Boghosian . |
| 4,424,234 | 1/1984 | Alderson et al. ........................ 424/317 |
| 4,686,211 | 8/1987 | Hara et al. ............................... 514/148 |

FOREIGN PATENT DOCUMENTS

| | | |
|---|---|---|
| 581587 | 2/1994 | European Pat. Off. . |
| 2279567 | 1/1995 | United Kingdom . |

*Primary Examiner*—William R. A. Jarvis
*Attorney, Agent, or Firm*—Pierce Atwood; Chris A. Caseiro

[57] ABSTRACT

One or more formulations for treating psoriasis and other skin disorders characterized by redness, itching, flaking, scaling, and plaque-type growth. The formulation includes a carrier component, one or more active ingredient components, and a surfactant component. The carrier preferably includes an alcohol in substantially equal volume with isopropyl myristate. The active ingredient component preferably includes a superpotent or high-potency corticosteroid such as clobetasol propionate, an anti-flaking ingredient such as zinc pyrithione, or a combination of the two. It may also include an anti-fungal compound. The surfactant component preferably includes an alkyl sulfate such as sodium lauryl sulfate. The formulations made by applied topically either in spray form or as a direct-contact liquid.

20 Claims, No Drawings

FORMULATION CONTAINING A CARRIER, ACTIVE INGREDIENT, AND SURFACTANT FOR TREATING SKIN DISORDERS

BACKGROUND OF THE INVENTION

1. Field of the Invention

The present invention relates to the treatment of psoriasis and other skin disorders characterized by redness, itching, flaking, scaling, and plaque-type growth. More particularly, the present invention relates to formulations for treating such disorders, in which the formulations include at least a carrier, an active ingredient, a surfactant to aid in emulsification/suspension, and an anti-fungal agent.

2. Description of the Prior Art

Skin disorders of great variety have plagued mankind for many years. Such skin disorders include, but are not limited to, psoriasis, eczema, lichenplanus, and seborrheic dermatitis (dandruff) and others related thereto. These disorders, to varying degrees, exhibit the following general characteristics: redness, itching, flaking, scaling, and plaque-type growth. Of course, such a brief description of the problem fails to indicate the extent of aggravation, embarrassment, and the like associated with such afflictions. Nevertheless, it is clear from the millions of dollars spent annually by afflicted individuals on prescription and over-the-counter treatments that this is a serious problem. Many treatments act only very temporarily on the symptoms and, often, not particularly effectively. While it may be possible to treat the underlying problem associated with some of the noted skin disorders, psoriasis presently has no known cure.

For the most part, the presently-available products that are reasonably effective in treating these disorders are often quite expensive. Those that are not so expensive, such as those popular products including hydrocortisone as the sole active ingredient, are simply not sufficiently effective in treating a broad group of sufferers. Moreover, those products that do provide some relief have a number of failings. One such product that has been available for a number of years is coal tar. It is terribly messy, has an undesirable odor, and stains the skin. Other prior-art products, such as those including the active ingredients salicylic acid, selenium sulfide, and sulfur, generally come in either creams or aerosol sprays. Unfortunately, the aerosol spray products are highly evaporative. As a result, they can cause a painful freezing sensation to the skin. A less likely, though important concern associated with the aerosol-applied treatments is the explosiveness of the products therein, particularly with regard to the use of propellants. Also, it is to be noted that those propellants serve no function in the treatment of the skin disorder, other than to force the active ingredient out of the container. The user is therefore paying for that component that is nothing but a delivery system. In fact, the propellant creates the undesirable freezing sensation associated with the delivery of the product in that cools upon expansion as it exits the container.

Those presently-available treatment products that are reasonably effective that are not delivered by aerosol spray are generally delivered to the skin in the form of a cream. While this eliminates the many noted problems associated with the aerosol sprays, there remain some problems with the creams. First, they may cause clogging of pores and therefore block delivery of a suitable quantity of the active ingredient to the epidermal layer. Additionally, the active ingredient may be bound or tied-up by numerous thickening agents commonly used in prior-art formulations. For those individuals who do not have an assistant to aid them in placing the treatment on the affected area, it can be difficult to apply a cream sufficient to adequately cover the problem area. Finally, creams, as with the aerosol sprays, generally cannot be measured out in fixed quantities. As a result, either inadequate treatment results, or excess product is used and therefore results, ultimately, in increased cost to the user.

One compound that has been found to be particularly effective in products for treating dandruff, specifically, and possibly eczema and psoriasis, is zinc pyrithione. While this compound is fairly effective, it is not so for a significant number of sufferers. That is, on the order of about 40% of the individuals suffering from the various skin disorders noted, zinc pyrithione is inadequate to alleviate the symptoms. A product offered by Cheminova International, S.A., of Spain and sold under the brand name Skin-Cap includes zinc pyrithione, and may well include other active ingredients. Unfortunately, this product is delivered by aerosol spray—with the failings associated therewith—and cannot be effectively applied as a topical spray or with a direct liquid applicator. It is therefore rendered less effective. It also lacks an anti-fungal agent, a potentially useful additive in light of indications that fungus may be a causal link in many skin conditions. In particular, there are strong indications that fungus and/or mold is present in a number of skin conditions including, but not limited to, psoriasis. Finally, with regard to the Skin-Cap product, it is simply not an option at the present time as it was recently banned and is not commercially available to skin disorder sufferers.

Other treatments available include the use of methotrexate, an oral drug, and light therapy. It is well known that methotrexate is toxic to the liver and therefore is of minimal usefulness to all but the most affected sufferer, and then only in restricted quantities. While the application of ultraviolet light has some effectiveness, it requires the patient to either go through the rigors of frequent trips to the doctor's office, or to purchase cumbersome and expensive equipment for in-home use. It can be seen then, that the presently existing means for treating a variety of skin disorders are ineffective, hazardous, irritating, and/or expensive.

Therefore, what is needed is one or more formulations suitable for the treatment of the skin conditions associated with disorders including, but not limited to, psoriasis, eczema, lichenplanus, and seborrheic dermatitis (dandruff) and others related thereto. Preferably, such formulations would include relatively inexpensive ingredients in order to render the treatment affordable. What is also needed is such a treatment that may be applied easily and uniformly, as in a topical treatment, with minimal dissociation of ingredients over a suitable period of time.

SUMMARY OF THE INVENTION

It is an object of the present invention to provide one or more formulations and methods of use suitable for the treatment of skin conditions associated with disorders including, but not limited to, psoriasis, eczema, lichenplanus, and seborrheic dermatitis (dandruff and others related thereto. It is also an object of the present invention to provide such treatments with relatively inexpensive ingredients in order to render the treatment affordable. It is further an object of the present invention to provide a skin-disorder treatment that may be applied easily, as in a topical treatment, with minimal dissociation of ingredients over a suitable period of time.

These and other objects are achieved in the present invention by the combination of three major components in order to create one or more skin-disorder treatments. The three major components include: 1) a carrier for delivering the active ingredient or ingredients of the formulation to the epidermis; 2) one or more active ingredients designed to treat the condition or conditions; and 3) one or more surfactants to ensure that the carrier and active components remain miscible or otherwise completely dispersed for a period of time suitable to get the active ingredient or ingredients below the upper epidermal layer. While the specific components may vary in strength and type, it is important that all three be used in the treatment formulation of the present invention. The resulting formulation provides for uniform and safe delivery of easy-to-measure amounts of the active ingredient or ingredients to the affected area.

The carrier preferably includes a blend of two compounds that aid in the miscibility—and "transferability" and absorption to and through the skin—of the various components of the formulations of the present invention. Each of the carrier components performs its function and together they offset the less-than-desirable characteristics associated therewith. The first carrier compound is an ester compound that acts as an emollient or solvent for the active ingredients to be described herein, In particular, the ester carrier may be a fatty-acid ester or an alcohol ester selected from the group including isopropyl myristate, isopropyl palmitate, octyl palmitate, octyl isononanoate, and isocetyl stearate.

While such ester compounds are beneficial in getting the active ingredient into solution and absorbed by the skin, and are desirable in a topical compound generally, they are somewhat oily and may clog the user's pores. In order to reduce those undesirable characteristics to ensure that the formulation remains solubilized, and to ensure that application of the formulation of the present invention on a user's skin will be uniformly dispersed and will evaporate over a reasonable period of time without drying the skin, an alcohol is included in the carrier component. The alcohol to be used is preferably any denatured alcohol, such as a denatured ethyl alcohol, or isopropyl alcohol, or other low-molecular weight compound, such as those with $C_2$–$C_6$ bases. In the preferred embodiment of the invention, the carrier compound is a blend of ethyl alcohol and isopropyl myristate. This blending of two compounds, rather than either one alone, allows the active ingredients to be described herein to penetrate into and be absorbed by the upper epidermal layer, while keeping the active component miscible and in suspension.

The active component of the treatment formulations of the present invention includes either a superpotent topical corticosteroid such as clobetasol propionate, augmented betamethasone diprorionate, or diflorasone diacetate, or a high-potency topical corticosteroid such as betamethasone valerate, betamethasone diproprionate, diflucortolone valerate, fluticasone valerate, hydrocortisone 17-butyrate, mometasone furoate, halobetasol propionate, desoximetasone, or flucinonide. These steroid compounds are beneficial in treating skin disorders; however, they must be used in relatively small concentrations and must form a portion of a prescribed formulation. The active component may also include the zinc pyrithione, coal tar, salicylic acid, selenium sulfide, or sulfur, compounds earlier noted as having been used with some nominal success in treating some types of skin disorders. These active compounds are known anti-bacterial, anti-flaking, compounds. Alternatively, or in addition to the above-identified active ingredients, a mild anti-fungal agent may be included in the formulation of the present invention. In particular, it has been noted that undecylenic acid may be such a suitable agent, combined with the other primary ingredients in a manner to be described herein.

The final key component of the present invention is the suspension-aiding surfactant. The surfactant may be any type of anionic surfactant that is preferably selected from the range of anionic surfactants including carboxylates such as soaps, alkyl aryl sulphonates, alkyl ether sulfates, alkyl sulfates, and alcohol sulfates. In particular, the anions of these surfactants, generally coupled to a cation such as sodium, potassium—even diethanolamine and triethanolamine in some instances—aid in the solubility of compounds with which they come in contact. These anionic surfactants are particularly useful in the formulations of the present invention in that they are more effective than other types of surfactants at the pH levels and desired stability associated with the active ingredients previously described. In the present invention, the surfactant is preferably the alkyl sulfate sodium lauryl sulfate. The surfactant or surfactants have a mild keratolytic action in that they may provide some benefit in reducing keratosis of the skin. Further, some of the anionic surfactants aid in ensuring that the carrier and active components will stay solubilized such that the treatment formulation will remain highly effective over a reasonable period of time.

The key of the present invention is the use of rather specific ratios of each of the three major components noted in creating the treatment formulations. That is, if too much of the carrier is used, the active ingredients will be proportionally less effective. Too much of the active ingredients makes application of the formulation less than optimal and, due to suspension and safety issues, may not be suitable. Too little of the surfactant will cause the active ingredient to dissociate from the mix such that, when the formulation is applied, varying concentrations, lack of uniform application, and/or incomplete contact with the skin area in distress will result. Therefore, based on the formula ratios to be described herein in the detailed description of the invention, as well as in the appended claims, the present invention results in topical formulations that are highly effective as skin disorder treatments. These formulations are essentially colorless, they have no lingering odor, they are non-staining, they are not hazardous, and may be applied in accurate amounts. These and other advantages of the present invention will become apparent to those skilled in this field upon review of the following detailed description of the preferred embodiments and the appended claims.

DETAILED DESCRIPTION OF THE PREFERRED EMBODIMENTS OF THE INVENTION

In the preferred embodiment of the present invention, the treatment formulation includes a surfactant component that is about 0.1% to about 2% by weight of the total formulation weight. Anything more than that will likely cause foaming and thickening of the formulation. The formulation also includes a primary active ingredient component that is about 0.01% to about 2% by weight of the total formulation weight, and the balance is made up of a carrier component. The carrier is preferably made of two compounds. These ratios of the three major components of the present invention result in a series of suitable formulations.

More specifically regarding the formulations of the present invention, the surfactant component is any type of anionic surfactant including carboxylates such as soaps, alkyl aryl sulphonates, alkyl ether sulfates, alkyl sulfates, and alcohol sulfates. Preferably, the anionic surfactant is sodium lauryl sulfate that may be as much as about 2% of the total formulation weight, and preferably it is about 0.1% of the total weight. The active component may also include, in addition to, or instead of, the primary active component, a secondary active component that is preferably an anti-fungal agent, undecylenic acid, that may be as much as about 10% of the total formulation weight, and is preferably about 0.3% of the total if used.

The active ingredient component is preferably a primary active component that is up to about 0.10% by weight of the total formulation weight of either a superpotent or a high-potency topical corticosteroid, and is preferably about 0.05% of the total formulation weight. A superpotent topical corticosteroid such as clobetasol propionate, augmented betamethasone diproprionate, or diflorasone diacetate, may be used. Alternatively, a high-potency topical corticosteroid such as betamethasone valerate, betamethasone diproprionate, diflucortolone valerate, fluticasone valerate, hydrocortisone 17-butyrate, mometasone furoate, halobetasol propionate, desoximetasone, or flucinonide may be used. The active ingredient component may also include, in addition to, or instead of, the corticosteroid, zinc pyrithione, coal tar, salicylic acid, selenium sulfide, or sulfur that may be as much as about 2% by weight of the total formulation weight, and is preferably about 0.25% by weight if used. The active component may also include, in addition to, or instead of, the primary active component, a secondary active component that is preferably a mild anti-fungal agent, undecylenic acid, that may be as much as about 10% of the total formulation weight, and is preferably about 0.3% of the total if used.

Finally, the carrier component makes up the balance of the total formulation weight and preferably includes any denatured alcohol, such as a denatured ethyl alcohol, or isopropyl alcohol, or other low-molecular weight compound, such as those with $C_2$–$C_6$ bases in combination with a fatty-acid ester or an alcohol ester selected from the group including isopropyl myristate, isopropyl palmitate, octyl palmitate, octyl isononanoate, and isocetyl stearate. The ratio of the fatty-acid ester or alcohol ester to the alcohol may range from as high as 95/5 to as low as about 50/50 by volume. Initially, the isopropyl alcohol, a commonly-available home-care product was used and found to be suitable. Subsequently, denatured ethyl alcohol was learned to be as effective and was less harsh to the skin and emitted less odor than the formulation with the isopropyl alcohol.

Formulations created with the noted components may be applied in either spray or liquid form to skin evidencing the effects of psoriasis, eczema, lichenplanus, and seborrheic dermatitis, and other disorders related thereto. When used over a period of 14 days, it has been determined that the preferred formulations reversed the skin conditions noted in substantially all users. More generally, a number of compound formulations were prepared and evaluated for applicability and effectiveness. Initially, the formulations were evaluated to determine whether there was suitable compound miscibility, dispersion and solubility. This evaluation was based on mixing the ingredients together, examining for solids suspension over a period of 24 hours and ensuring that the viscosity of the mix was low enough for it to be sprayed by finger pump without the use of a propellant. That determination was made by evaluating the ability to create a mist pattern upon spraying, which mist pattern was preferably similar to that of water. It was immediately determined that the fatty-acid esters and alcohol esters of the carrier component would not permit the creation of such a mist pattern; however, when combined with noted alcohols, such a pattern was achieved. Application of the present invention substantially ensures a uniform dispersion of the active component or components with minimal loss of compound.

Once the first of the evaluated formulations exhibited stable solubility and "sprayability" over a period of time leading to an indication of a product shelf life of at least one year with acceptable sprayability, it was applied to the afflicted areas of the skin of 13 test patients. The patients were examined by a physician for reductions in redness, itching, flaking, scaling, and plaque-type growth of the skin. A positive result was signified by a reduction in the particular affliction. That first formulation included as the active ingredient the zinc pyrithione without the corticosteroid. Seven of the 13 patients exhibited positive results. A second version of the formulation of the present invention included the corticosteroid and 11 of the 13 patients exhibited positive results. Variations on the formulations found to be most effective are presented in Tables 1 to 6.

TABLE 1

| Compound | Weight Percent |
| --- | --- |
| Isopropyl Myristate/Isopropyl Alcohol (50/50 by vol.) | 99.65 |
| Isopropyl Myristate/Ethyl Alcohol (50/50 by vol.) | 0.0 |
| Clobetasol Propionate | 0.0 |
| Zinc Pyrithione | 0.25 |
| Sodium Lauryl Sulfate | 0.1 |
| Undecylenic Acid | 0.0 |
| Results: Sprayable; strong, undesirable odor of alcohol; harsh to skin; positive results in approximately 30% of patients tested. | |

TABLE 2

| Compound | Weight Percent |
| --- | --- |
| Isopropyl Myristate/Isopropyl Alcohol (50/50 by vol.) | 0.0 |
| Isopropyl Myristate/Ethyl Alcohol (50/50 by vol.) | 99.65 |
| Clobetasol Propionate | 0.0 |
| Zinc Pyrithione | 0.25 |
| Sodium Lauryl Sulfate | 0.1 |
| Undecylenic Acid | 0.0 |
| Results: Sprayable; reduction in the number of complaints of skin irritation; positive results in approximately 35% of patients tested. | |

TABLE 3

| Compound | Weight Percent |
| --- | --- |
| Isopropyl Myristate/Isopropyl Alcohol (50/50 by vol.) | 0.0 |
| Isopropyl Myristate/Ethyl Alcohol (50/50 by vol.) | 99.6 |
| Clobetasol Propionate | 0.05 |
| Zinc Pyrithione | 0.25 |
| Sodium Lauryl Sulfate | 0.1 |
| Undecylenic Acid | 0.0 |
| Results: Sprayable; no lingering odor; no complaints of harshness; positive results in approximately 80% of patients tested. | |

TABLE 4

| Compound | Weight Percent |
| --- | --- |
| Isopropyl Myristate/Isopropyl Alcohol (50/50 by vol.) | 99.6 |
| Isopropyl Myristate/Ethyl Alcohol (50/50 by vol.) | 0.0 |
| Clobetasol Propionate | 0.05 |
| Zinc Pyrithione | 0.25 |
| Sodium Lauryl Sulfate | 0.1 |

TABLE 4-continued

| Compound | Weight Percent |
| --- | --- |
| Undecylenic Acid | 0.0 |

Results: Sprayable; complaints of lingering alcohol odor and harshness to the skin; positive results in approximately 75% of patients tested.

TABLE 5

| Compound | Weight Percent |
| --- | --- |
| Isopropyl Myristate/Isopropyl Alcohol (50/50 by vol.) | 99.3 |
| Isopropyl Myristate/Ethyl Alcohol (50/50 by vol.) | 0.0 |
| Clobetasol Propionate | 0.05 |
| Zinc Pyrithione | 0.25 |
| Sodium Lauryl Sulfate | 0.1 |
| Undecylenic Acid | 0.3 |

Results: Sprayable; complaints of lingering alcohol odor and harshness to the skin; positive results in approximately 80% of patients tested.

TABLE 6

| Compound | Weight Percent |
| --- | --- |
| Isopropyl Myristate/Isopropyl Alcohol (50/50 by vol.) | 0.0 |
| Isopropyl Myristate/Ethyl Alcohol (50/50 by vol.) | 99.3 |
| Clobetasol Propionate | 0.05 |
| Zinc Pyrithione | 0.25 |
| Sodium Lauryl Sulfate | 0.1 |
| Undecylenic Acid | 0.3 |

Results: Sprayable; no complaints associated with odor or harshness; positive results in more than 90% of patients tested.

It is to be understood that the present invention has been described with specific reference to preferred formulations. It is intended that those formulations, their variants and equivalents are covered hereby with reference to the following appended claims.

I claim:

1. A formulation for treating skin disorders consisting essentially of:
   a. about 0.01% to about 2% by weight of an active ingredient compound selected from the group consisting of clobetasol propionate, augmented betamethasone diproprionate, diflorasone diacetate, betamethasone valerate, betamethasone diproprionate, diflucortolone valerate, fluticasone valerate, hydrocortisone 17-butyrate, mometasone furoate, halobetasol propionate, desoximetasone, flucinonide, zinc pyrithione, coal tar, salicylic acid, selenium sulfide, and sulfur;
   b. 0.1% to about 2% by weight of an anionic surfactant compound selected from the group consisting of soap, alkyl aryl sulphonate, alkyl ether sulfate, alkyl sulfate, and alcohol sulfate;
   c. 0.3% to about 10% by weight of undecylenic acid; and
   d. a carrier compound to make up the balance of weight of said formulation, said carrier compound formed of a combination of two components in a volume ratio of about 50/50, wherein a first carrier component of said combination of two components is selected from the group consisting essentially of ethyl alcohol and isopropyl alcohol and a second carrier component of said combination of two components is selected from the group consisting essentially of isopropyl myristate, isopropyl palmitate, octyl palmitate, octyl isononanoate, and isocetyl stearate.

2. The formulation as claimed in claim 1 wherein said first carrier component is ethyl alcohol and said second carrier component is isopropyl myristate.

3. The formulation as claimed in claim 1 wherein said first carrier component is isopropyl alcohol and said second carrier component is isopropyl myristate.

4. The formulation as claimed in claim 1 wherein said active ingredient compound is about 0.05% by weight of clobetasol propionate and about 0.25% by weight of zinc pyrithione.

5. The formulation as claimed in claim 4 wherein said anionic surfactant compound is about 0.1% by weight of sodium lauryl sulfate, the formulation including about 0.3% by weight of undecylenic acid.

6. The formulation as claimed in claim 1 wherein said anionic surfactant compound is about 0.1% by weight of sodium lauryl sulfate, the formulation including about 0.3% by weight of undecylenic acid.

7. The formulation as claimed in claim 6 wherein said active ingredient compound is about 0.05% by weight of clobetasol propionate and about 0.25% by weight of zinc pyrithione.

8. A formulation for treating skin disorders consisting essentially of:
   a. about 0.01% to about 0.10% by weight of clobetasol propionate;
   b. 0.1% to about 2% by weight of an anionic surfactant compound selected from the group consisting of soap, alkyl aryl sulphonate, alkyl ether sulfate, alkyl sulfate, and alcohol sulfate;
   c. 0.3% to about 10% by weight of undecylenic acid; and
   d. a carrier compound to make up the balance of weight of said formulation, said carrier compound formed of a combination of two components in a volume ratio of about 50/50, wherein a first carrier component of said combination of two components is selected from the group consisting essentially of ethyl alcohol and isopropyl alcohol and a second carrier component of said combination of two components is isopropyl myristate.

9. The formulation as claimed in claim 8 consisting of about 0.05% by weight of clobetasol propionate.

10. The formulation as claimed in claim 8 wherein said anionic surfactant compound is about 0.1% by weight of sodium lauryl sulfate.

11. The formulation as claimed in claim 10 including about 0.3% by weight of undecylenic acid.

12. The formulation as claimed in claim 8 wherein said first carrier component is ethyl alcohol.

13. The formulation as claimed in claim 8 wherein said first carrier component is isopropyl alcohol.

14. A formulation for treating skin disorders consisting essentially of:
   a. about 0.01% to about 2% by weight of zinc pyrithione;
   b. 0.1% to about 12% by weight of an anionic surfactant compound selected from the group consisting of soap, alkyl aryl sulphonate, alkyl ether sulfate, alkyl sulfate, and alcohol sulfate;
   c. 0.3% to about 10% by weight of undecylenic acid; and
   d. a carrier compound to make up the balance of weight of said formulation, said carrier compound formed of a combination of two components in a volume ratio of about 50/50, wherein a first carrier component of said combination of two components is selected from the group consisting essentially of ethyl alcohol and isopropyl alcohol and a second carrier component of said combination of two components is isopropyl myristate.

15. The formulation as claimed in claim 14 consisting of about 0.25% by weight of zinc pyrithione.

16. The formulation as claimed in claim 14 wherein said anionic surfactant compound is about 0.1% by weight of sodium lauryl sulfate.

17. The formulation as claimed in claim 16 including about 0.3% by weight of undecylenic acid.

18. The formulation as claimed in claim 14 wherein said first carrier component is ethyl alcohol.

19. The formulation as claimed in claim 14 wherein said first carrier component is isopropyl alcohol.

20. The formulation as claimed in claim 14 further comprising about 0.05% by weight of clobetasol propionate.

* * * * *